US010702346B2

United States Patent
Popovic et al.

(10) Patent No.: US 10,702,346 B2
(45) Date of Patent: Jul. 7, 2020

(54) IMAGE INTEGRATION AND ROBOTIC ENDOSCOPE CONTROL IN X-RAY SUITE

(71) Applicant: KONINKLIJKE PHILIPS N.V., Eindhoven (NL)

(72) Inventors: Aleksandra Popovic, Boston, MA (US); Aryeh Leib Reinstein, Bronx, NY (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 632 days.

(21) Appl. No.: 15/324,001

(22) PCT Filed: Jul. 14, 2015

(86) PCT No.: PCT/IB2015/055305
§ 371 (c)(1),
(2) Date: Jan. 5, 2017

(87) PCT Pub. No.: WO2016/009339
PCT Pub. Date: Jan. 21, 2016

(65) Prior Publication Data
US 2017/0196643 A1 Jul. 13, 2017

Related U.S. Application Data

(60) Provisional application No. 62/024,532, filed on Jul. 15, 2014.

(51) Int. Cl.
*A61B 34/30* (2016.01)
*A61B 34/20* (2016.01)
(Continued)

(52) U.S. Cl.
CPC ............... *A61B 34/30* (2016.02); *A61B 1/04* (2013.01); *A61B 6/12* (2013.01); *A61B 34/20* (2016.02);
(Continued)

(58) Field of Classification Search
None
See application file for complete search history.

(56) References Cited

U.S. PATENT DOCUMENTS 9,095,252 B2  8/2015  Popovic
9,205,564 B2  12/2015  Popovic
(Continued)

FOREIGN PATENT DOCUMENTS

| WO | 2011086431 A1 | 7/2011 |
| WO | 2013080124 A1 | 6/2013 |
| WO | 2014001948 A2 | 1/2014 |

*Primary Examiner* — Joanne M Hoffman (57) ABSTRACT

A workstation for calibrating a robotic instrument (42) has a distal tip (46) within an X-ray image space (35) of an X-ray modality (32). The workstation employs a calibration controller (50) for calibrating a remote center of motion (RCM) length of the robotic instrument (42) responsive to X-ray images (36) of different poses of the distal tip (46) of the robotic instrument (42) within the X-ray image space (35), and further employs a robotic instrument controller (40) for controlling a guidance of the robotic instrument (42) within the X-ray image space (35) from the RCM calibration. The robotic instrument (42) may include an endoscope whereby the calibration controller (50) is further employed to calibrate a focal length of the robotic instrument (42) responsive to the X-ray images (36) and one or more endoscope image(s) (48) of the X-ray image space (35) for controlling the guidance of the robotic instrument (42) within the X-ray image space (35) from the RCM/focal length calibrations.

18 Claims, 8 Drawing Sheets

(51) Int. Cl.
   *A61B 1/04*    (2006.01)
   *A61B 6/12*    (2006.01)
   *A61B 90/00*   (2016.01)

(52) U.S. Cl.
   CPC ... *A61B 2034/301* (2016.02); *A61B 2090/062* (2016.02); *A61B 2090/376* (2016.02); *A61B 2560/0223* (2013.01)

(56) References Cited

U.S. PATENT DOCUMENTS

| | | | | |
|---|---|---|---|---|
| 2003/0120283 | A1* | 6/2003 | Stoianovici | A61B 34/70 606/130 |
| 2006/0036162 | A1* | 2/2006 | Shahidi | A61B 5/06 600/424 |
| 2008/0171936 | A1* | 7/2008 | Homan | A61B 6/4441 600/424 |
| 2010/0240989 | A1* | 9/2010 | Stoianovici | A61B 34/70 600/429 |
| 2010/0274087 | A1* | 10/2010 | Diolaiti | A61B 90/37 600/118 |
| 2012/0071752 | A1* | 3/2012 | Sewell | A61B 6/12 600/424 |
| 2014/0046128 | A1* | 2/2014 | Lee | A61B 1/00009 600/102 |
| 2014/0142422 | A1* | 5/2014 | Manzke | A61B 8/0841 600/424 |
| 2014/0264081 | A1* | 9/2014 | Walker | G01B 11/14 250/459.1 |
| 2014/0276937 | A1* | 9/2014 | Wong | A61B 17/00 606/130 |
| 2014/0347353 | A1 | 11/2014 | Popovic | |
| 2015/0112126 | A1* | 4/2015 | Popovic | A61B 1/00009 600/36 |
| 2015/0190204 | A1* | 7/2015 | Popovi | A61B 34/20 600/424 |
| 2015/0320514 | A1* | 11/2015 | Ahn | A61B 34/30 606/130 |

\* cited by examiner

ENDOSCOPE OVERLAY
142

FIG. 9C

X-RAY ↔ ENDOSCOPE BLENDING
143

FIG. 9D

IMAGE INTEGRATION AND ROBOTIC ENDOSCOPE CONTROL IN X-RAY SUITE

CROSS-REFERENCE TO PRIOR APPLICATIONS

This application is the U.S. National Phase application under 35 U.S.C. § 371 of International Application No. PCT/IB2015/055305, filed on Jul. 14, 2015, which claims the benefit of U.S. Provisional Patent Application No. 62/024,532, filed on Jul. 15, 2014. These applications are hereby incorporated by reference herein.

FIELD OF THE INVENTION

The present invention generally relates to utilizing X-ray images acquired during a minimally invasive procedure (e.g., cardiac surgery, laparoscopic surgery, natural orifice transluminal surgery, single incision laparoscopic surgery, pulmonary/bronchoscopy surgery and diagnostic interventions) to perform calibration procedures for a robotic endoscope. The present invention more particularly relates to an integration of X-ray/endoscope images for guiding the robotic endoscope during the minimally invasive procedure.

BACKGROUND OF THE INVENTION

Minimally invasive surgery is performed using elongated instruments inserted into the patient's body through small ports. The main visualization method during these procedures is an endoscope. In robotic guided minimally invasive surgery, one or more of the instruments is held and controlled by a robotic device, particularly the endoscope.

Specifically, the small ports that are placed on the patient's body are the only incision points through which the instruments and endoscope may pass to access the inside of the patient. As such, the instruments can rotate around these fulcrum points, but they cannot impose translational forces on the ports, as this would cause injury and harm to the patient. This is especially important for robotic guided surgery, as the robot may potentially exert large forces.

As such, some known robots implement what is known as a remote center of motion (RCM) at the fulcrum point by enforcing that only rotation may be performed at the port and all translational forces at the port are eliminated. This can be achieved by implementing a mechanical design which has a remote center of motion at a specific location in space, and then aligning that point in space with the port.

Once the endoscope is inserted into the patient's body and an appropriate location of RCM is selected, the robot can be controlled from endoscope images. To close that control loop, a mathematical transformation between image coordinates and robot joint space has to be established (referred to in the art as Image Jacobian). The entire process is referred to in the art as the system calibration and requires various steps such as camera and robot calibration. Furthermore, to provide full calibration, depth between the camera and the organ/object under consideration needs to be measured and such measurements are typically either from images or using special sensors.

Intraoperative X-ray imaging may be used to supplement endoscopy during the procedure. For example, for minimally invasive coronary bypass surgery, intraoperative X-ray is used to identify arterial sclerosis or to confirm revascularization. As this imaging modality uses ionizing radiation, it is beneficial for the patient and the operation room staff that the number of X-ray images acquired during the procedure is reduced.

In order to improve utility of both imaging modalities, the system has to allow target cross-identification between the modalities. For example, if an arterial stenosis is not visible in an endoscope image and is visible in an X-ray image, a method to integrate these images and depict the stenosis in the endoscope image would greatly improve the workflow and reduce both operation time and reduce likelihood of complications. Further, control of the endoscope from X-ray images would lead to better visualization and detection of targets outside of endoscope's field-of-view.

In order to perform all these integrations, a calibration of endoscope as well as calibration of the robot has to be performed. The process to calibrate a robot and endoscope in the operating theater is tied to various issues.

One issue is camera calibration is an additional step that needs to be performed prior to the surgery by a trained person. This process is time-consuming and error prone.

A second issue is, if the user changes some of the camera parameters during surgery (e.g., zoom), then the endoscope has to be removed from the patient and recalibrated which might not be acceptable as it would interrupt the workflow.

A third issue is, if the user moves endoscope relative to the robot (e.g., inserts deeper into the body to perform mechanical zoom with a common class of endoscope that do not have optical zoom), then the system has to be either recalibrated or the robot must utilize additional sensors.

A fourth issue is calibration may require depth information, which might be accessible using depth finding algorithms (e.g., shape from motion or similar), but those kind of measurements are usually noisy, which might cause instability.

These issues may reduce usability of the system and disturb the workflow which will lead to an increase of procedure cost and lower acceptance rate.

SUMMARY OF THE INVENTION

The present invention provides a calibration controller for performing a series of calibrations of a robotic instrument from X-ray images acquired during a minimally invasive procedure (e.g., cardiac surgery, laparoscopic surgery, natural orifice transluminal surgery, single incision laparoscopic surgery, pulmonary/bronchoscopy surgery and diagnostic interventions).

The present invention further provides the calibration controller for integrating X-ray/endoscope images as well as to facilitate a guidance of the robotic endoscope from the X-ray images.

One form of the present invention is a workstation for calibrating a robotic instrument having a distal tip within an X-ray image space of an X-ray modality. The workstation employs a calibration controller for calibrating an RCM length of the robotic instrument responsive to generation by the X-ray modality of a plurality of X-ray images of different poses of the distal tip of the robotic instrument within the X-ray image space. The workstation further employs a robotic instrument controller for controlling a guidance of the robotic instrument within the X-ray image space as a function of the calibration by the calibration controller of the RCM length of the robotic instrument.

For purposes of the present invention, terms of the art including, but not limited to, "workstation", "calibration", "X-ray image", "X-ray image space", X-ray modality", "focal tip", "pose", and "guidance" are to be interpreted as understood in the art of the present invention and as exemplary described herein.

For purposes of the present invention, (1) the term "robotic instrument" broadly encompass all structural configurations of an instrument held by a spherical robot, (2) the term "instrument" broadly encompasses any and all instruments, tools, etc. utilized during minimally invasive procedures as known in the art including, but not limited to, scopes, graspers, cutters and ultrasound probes of any type.

(3) the term "spherical robot" broadly encompasses any robotic device structurally configured with motorized control of one or more joints concentrically connecting arm segments for implementing a remote-center-of-motion ("RCM") as understood in the art of the present invention and as exemplary described herein, and (4) the term "RCM length" broadly encompasses a length of a distance between a RCM of the spherical robot and a distal tip of the instrument being held by the spherical robot as understood in the art of the present invention and as exemplary described herein.

A second form of the present invention involves the robotic instrument exclusively or inclusively including an endoscope, and the workstation employing the calibration controller for calibrating a focal length of the robotic instrument responsive to a generation by the X-ray modality of the aforementioned X-ray images and further responsive to a generation by the robotic instrument of one or more endoscope images of the X-ray image space.

From the calibration of the RCM length and the focal length of the robotic instrument, the calibration controller may further control an image integration of the X-ray images and the endoscope image(s) for display.

For purposes of the present invention, terms of the art further including, but not limited to, "endoscope image", "image integration" and "display" are to be interpreted as understood in the art of the present invention and as exemplary described herein.

For purposes of the present invention, the term "endoscope" broadly encompasses any device structurally configured with ability to image from inside a body as understood in the art of the present invention and as exemplary described herein.

Examples of an endoscope include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, colposcope, thoracoscope, sygmoidscope, neuroendoscope, etc.) and any device similar to a scope that is equipped with an image system). The imaging is local, and surface images may be obtained optically with fiber optics, lenses, and miniaturized (e.g. CCD based) imaging systems (e.g., laparoscopic ultrasound).

For purposes of the present invention, the term "focal length" broadly encompasses a length of the field-of-view of the endoscope extending from the distal focal tip as understood in the art of the present invention and as exemplary described herein.

For purposes of the present invention, the term "controller" broadly encompasses all structural configurations of an application specific main board or an application specific integrated circuit housed within or linked to a workstation for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot(s) and port(s).

Examples of the workstation include, but are not limited to, an assembly of one or more computing devices (e.g., a client computer, a desktop and a tablet), a display/monitor, and one or more input devices (e.g., a keyboard, joysticks and mouse).

A third form of the present invention is the calibrator controller employing application modules in the form of a robotic instrument calibrator for calibrating the RCM length and the focal length of the robotic instrument responsive to the X-ray images and the endoscope image(s), and an image integrator for integrating the X-ray images and the endoscope image(s) responsive to the calibration by the robotic endoscope calibrator of the RCM length and the focal length of the robotic instrument.

For purposes of the present invention, the term "application module" broadly encompasses a component of the controller consisting of an electronic circuit and/or an executable program (e.g., executable software and/or firmware) for executing a specific application.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

Figure 1:
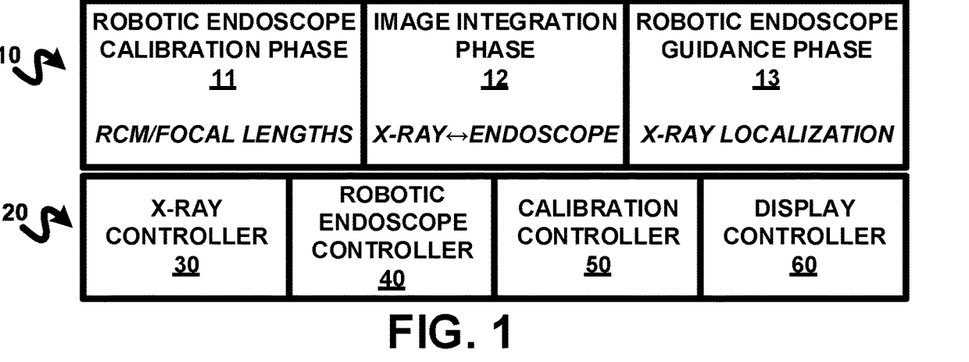
FIG. 1 illustrates an exemplary embodiment of a minimally invasive procedure and controller suite in accordance with the inventive principles of the present invention.
Figure 2:
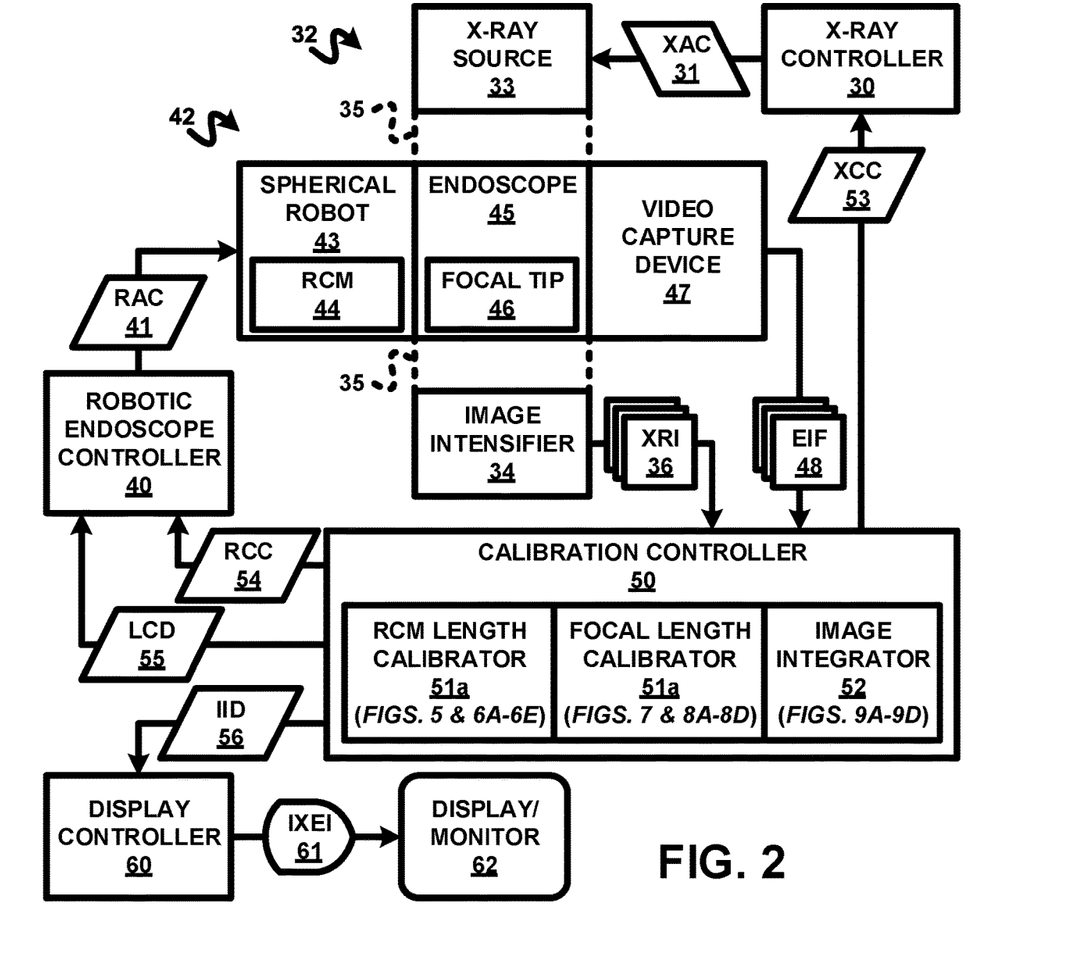
FIG. 2 illustrates an exemplary embodiment of a minimally invasive control system in accordance with the inventive principles of the present invention.

To facilitate an understanding of the present invention, the following description of FIGS. 1 and 2, teaches basic inventive principles of an image-based robotic endoscope control scheme 10 for a minimally invasive procedure accomplished by a controller network 20. For purposes of the present invention, the term "robotic endoscope" broadly encompasses all structural configurations of an endoscope held by a spherical robot. From this description, those having ordinary skill in the art will appreciate how to apply the inventive principles of the present invention to various minimally invasive procedures incorporating robotic instruments excluding or including an endoscope.

Referring to FIG. 1, control scheme 10 includes a robotic endoscope calibration phase 11, an image integration phase 12, and a robotic endoscope guidance phase 13.

Generally, robotic endoscope calibration phase 11 involves an acquisition of X-ray images of a distal focal tip of a robotic endoscope within an X-ray image space for purposes of calibrating an RCM length and an focal length of a robotic endoscope as will be further described herein in connection with FIG. 2.

From the calibrations, image integration phase 12 involves an integration of the X-images and endoscope images for purposes of facilitating an X-ray localization of anatomical target(s) during a minimally invasive procedure as will be further described herein in connection with FIG. 2.

From the image integration, robotic endoscope guidance phase 13 involves an X-ray guidance of the robotic endoscope to an anatomical target whereby the target may be centered in the endoscope image as will be further described herein in connection with FIG. 2.

To implement control scheme 10, controller network 20 employs an X-ray controller 30, a robotic endoscope controller 40, a calibration controller 50 and a display controller 60.

X-ray controller 30 is structurally configured as known in the art for controlling an operation of X-ray modality, robotic endoscope controller 40 is structurally configured as known in the art for controlling an operation of a robotic endoscope, and display controller 60 is structurally configured as known in the art for controlling an operation of a display/monitor.

Calibration controller 50 is structurally configured in accordance with the inventive principles of the present invention for controlling a calibration of the RCM length and the focal length of a robotic endoscope as will be further described herein in connection with FIG. 2.

In practice, controller network 20 may be incorporated within a single workstation or distributed in any manner among multiple workstations.

FIG. 2 illustrates an exemplary implementation of control scheme 10 by controller network 20.

Referring to FIGS. 1 and 2, X-ray controller 30 generates X-ray actuation commands 31 for controlling an operation of an X-ray modality 32 employing an X-ray source 33 and an image intensifier 34 as understood in the art for acquiring X-images 36 of an X-ray image space 35 extending between X-ray source 33 and image intensifier 34.

Robotic endoscope controller 40 generates robotic actuation commands 41 for controlling an operation of a robotic endoscope 42 structurally defined by an endoscope 45 being held by a spherical robot 43 for acquiring an endoscopic video signal via a distal focal tip 46 of endoscope 45 as understood in the art. More particularly, spherical robot 43 structurally establishes a remote-center-of-motion 44 aligned with distal focal tip 46 along an elongated axis of endoscope 45. A video capture device 47 is provided with a capability to convert the endoscopic video signal from endoscope 45 as understood in the art into a computer readable temporal frame sequence of endoscope images ("EIF") 48. In practice, video capture device 47 may employ a frame grabber of any type for capturing individual digital still frames from the endoscopic video signal.

The RCM length is a distance between RCM 44 of spherical robot 43 and distal focal tip 46 of endoscope 45, and the focal length is a length of field-of-view of endoscope 45 extending from distal focal tip 46 as understood in the art, which lengths are unknown prior to the implementation of robotic endoscope calibration phase 11.

For calibrating the lengths during phase 11, calibration controller 50 employs a robotic endoscope calibrator 51 including a RCM length calibrator 51a for calibrating the RCM length, and a focal length calibrator 51b for calibrating the focal length of robotic endoscope 42. In practice, robot endoscope calibrator 51 may generate X-ray calibration commands 53 to X-ray controller 30 for commanding a specific positioning of X-image space 35 within an X-ray coordinate space as understood in the art, and/or may generate robot calibration commands 54 to robotic endoscope controller 40 for commanding a specific positioning of robotic endoscope 42 within a robot coordinate space of spherical robot 43 as known in the art.

Display controller 60 controls an operation of a display/monitor 62 for illustrating X-ray images 35 and endoscope images 47, individually or integrated as understood in the art. As to the integrated images, calibration controller 50 further employs an image integrator 52 for integrating X-ray images 36 and endoscope images 48 based on the calibrated lengths. From the image integration, image integrator 52 provides image integration data 56 to display controller 60 whereby display controller 60 generates an integrated X-ray/endoscope image 61 for display by display/monitor 62.

Still referring to FIGS. 1 and 2, the following is a description of an implementation of control scheme 11 by controller network 20.

Robotic Endoscope Calibration Phase 11.

The length calibrations are performed by robotic endoscope calibrator 51 from X-ray images 36 of different poses of the distal focal tip 46 of endoscope 45 within X-ray image space 35.

In practice, endoscope 45 may be the only object within X-ray image space, or may be accompanied by another object (e.g., a phantom anatomical object) and/or a patient. With a patient, preferably X-images 36 are acquired during a diagnostic procedure without any need for introducing additional ionizing radiation to the patient.

In practice, X-ray controller 30 may be user commanded or responsive to X-ray calibration commands 53 from robotic endoscope calibrator 51 to position X-ray source 33 and image intensifier 34 as needed to acquire X-ray images 36 of different poses of the distal focal tip 46 of endoscope 45 within X-ray image space 35. The length calibrations may be performed during (i.e., on-the-fly) or subsequent to the acquisition of X-ray images 36. Additionally, robotic endoscope controller 40 may be user commanded or responsive to robot calibration commands 54 from robotic endoscope calibrator 51 to position distal focal tip 46 in different poses within X-ray image space 35 as needed to support the length calibrations.

For the RCM length calibration, RCM length calibrator 51a processes two (2) or more X-ray images 36 as will be further described herein in connection with FIGS. 5 and 6A-E. For the focal length calibration, focal length calibrator 51b processes three (3) or more X-ray images 36 as will be further described herein in connection with FIGS. 7 and 8A-8D. In practice, calibrators 51a and 51b may sequentially or concurrently execute the length calibrations. Furthermore, calibrators 51a and 51b execute initial length calibrations that may be recalibrated or refined with additional X-ray images 36.

Image Integration Phase 12.

The image integration is performed by image integrator 52 at any time during and/or subsequent to the length calibrations.

In practice, any known image integration technique may be implemented by image integrator 52 during phase 12 including, but not limited, a X-ray point projection technique, an endoscope point projections technique, an endoscope overlay on X-ray technique and an X-ray/endoscope image blending technique as further described herein in connection with FIGS. 9A-9D.

Robotic Endoscope Guidance Phase 13.

The guidance of robotic endoscope 42 is performed by robotic endoscope controller 40 via a processing of length calibration data 55 informative of the length calibrations and provided by robotic endoscope calibrator 51 upon completion of the initial length calibrations and any recalibration thereof and during any refined calibrations.

In practice, any known robot guidance technique may be implemented by robot endoscope controller 40 during phase 13 including, but not limited to, any technique involving a selection of a target point in an X-ray image 36 whereby robot endoscope controller 40 generates robot actuation commands 41 to position distal focal tip 46 within X-ray image space 35 having the target point centered within endoscope image 48.

Minimally Invasive Procedure.

In practice, phases 11 and/or 12 may be performed prior to and/or during an execution of a minimally invasive procedure incorporating phase 13. As such, the length calibrations by calibration controller 50 during phase 11 may be user-initiated or responsive to an initial acquisition of X-ray images 36. In either case, control network 20 may execute as needed a safety measure of preventing a performance of the minimally invasive procedure until after initial length calibrations.

Figure 3:
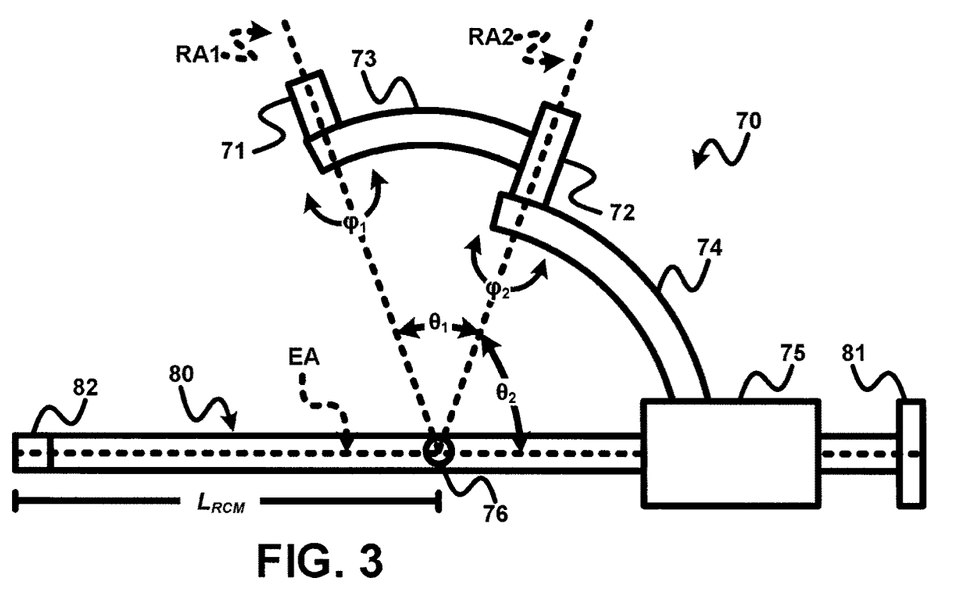
FIG. 3 illustrates an exemplary embodiment of a robotic endoscope in accordance with the inventive principles of the present invention.

To facilitate a further understanding of the present invention, the following description of FIGS. 3-9, teaches basic inventive principles of length calibration methods incorporating a robotic endoscope shown in FIG. 3. From this description, those having ordinary skill in the art will appreciate how to apply the inventive principles of the length calibration methods to alternative robot endoscopes.

Referring to FIG. 3, a spherical robot 70 employs an actuator 71 having a rotation axis RA1, an actuator 72 having a rotation axis RA2, a support arc 73, and an instrument arc 74 including an end-effector 75 for holding a metallic endoscope 80 having a rotation axis EA. Support arc 73 is concentrically connected to actuator 71 and actuator 72, and instrument arc 74 is concentrically connected to actuator 72. Of importance, (1) rotational axes RA1, RAD and EA intersect at a remote center of motion 76 of spherical robot 70,
(2) a base arch length of $\theta_B$ of support arc 73 extends between rotation axes RA1 and RA2,
(3) an extension arc length $\theta_{E1}$ of instrument arc 74 extends between rotation axes RA1 and EA,
(4) actuator 71 may be commanded to co-rotate arcs 73 and 74 about rotation axis RA1 for a desired $\varphi_1$ degrees to control a broad movement of distal focal tip 82 of endoscope 80,
(5) actuator 72 may be commanded to rotate instrument arc 74 about rotation axis RA2 for a desired $\varphi_2$ degrees to control a targeted movement of distal focal tip 82 of endoscope 80,
(6) end effector 75 has a capability, manual or controlled, of rotating endoscope 80 about its rotation axis EA,
(7) an RCM length $L_{RCM}$ is a distance between RCM 76 and distal focal tip 82, and
(8) an focal length (not shown) is a length of a field-of-view of the endoscope 80 extending from distal focal tip 83 as viewable from an eyepiece 81 of endoscope 80.

Figure 4:
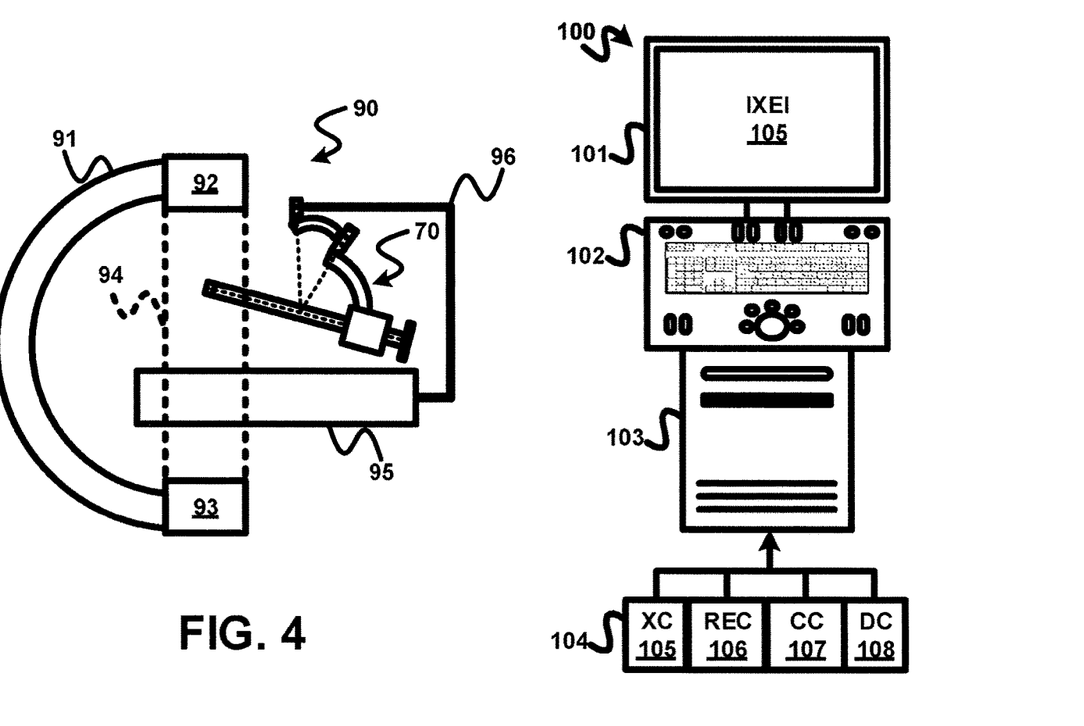
FIG. 4 illustrates an exemplary embodiment of a workstation based minimally invasive control system in accordance with the inventive principles of the present invention.

Referring to FIGS. 3 and 4, an X-ray modality 90 employs a C-arm 91 aligning an X-ray source 92 and an image intensifier 93 for establishing an X-ray image space 94. Robot 70 is mounted to a passive arm 96 attached to an X-ray table 95 whereby distal focal tip 82 is positioned within X-ray image space 94, and whereby RCM 76 may or may not be positioned within X-ray image space 94.

Still referring FIGS. 3 and 4, a calibration workstation 100 employs a monitor 101, an interface platform 102 (e.g., keyboard, buttons, dials, joysticks, etc.), a client computer 103, and a controller network 104 installed within workstation computer 103.

Controller network 104 includes an X-ray controller 105, a robotic endoscope controller 106, a calibration controller 107 and a display controller 108. In practice, controllers 105-108 may be segregated and/or integrated to any degree within client computer 103. Alternatively, X-ray controller 105 may be installed within a workstation (not shown) of X-ray modality 90 and endoscope controller 106 may be installed within a workstation (not shown) of robot 70 whereby client computer 103 provides user interfaces via monitor 101 and user interface 102 for accessing X-ray controller 105 and/or endoscope controller 106 as needed. For such an alternative, a display controller 108 may be installed in each workstation.

Workstation computer 103 is connected/coupled to spherical robot 70, endoscope 80 and X-ray modality 90 to facilitate an implementation of length calibration methods by controller network 104 as will now be described herein in connection with FIGS. 5-9D.

Figure 5:
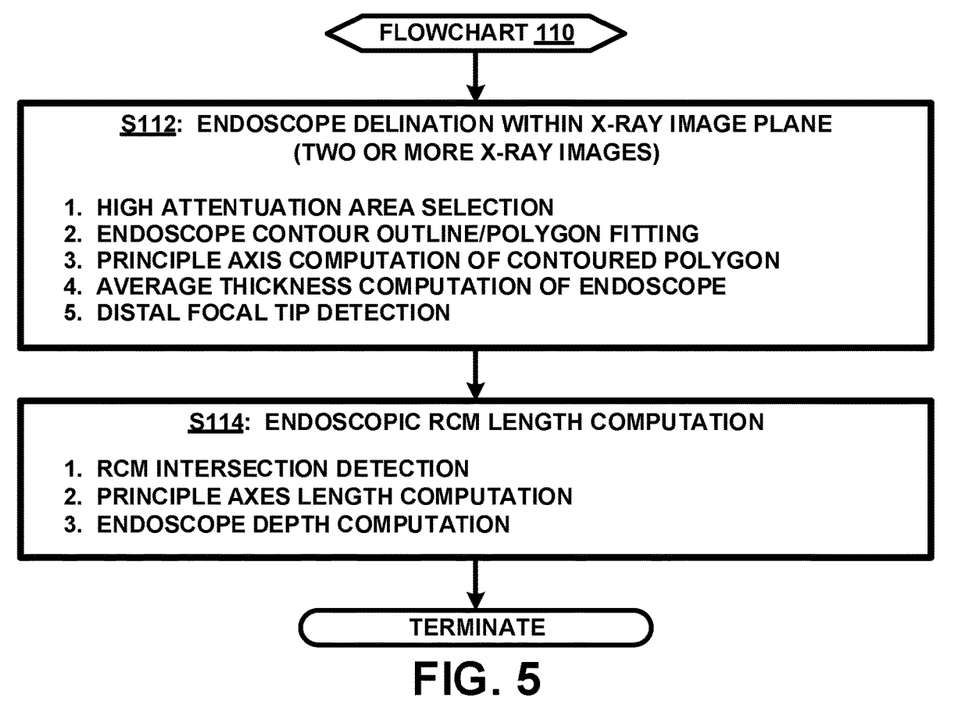
FIG. 5 illustrates a flowchart representative of an exemplary embodiment of an RCM length computation method in accordance with the inventive principles of the present invention.

FIG. 5 illustrates a flowchart 110 representative of an RCM length calibration method of the present invention.

Referring to FIGS. 3-5, two (2) exemplary X-ray images 97(X1) and 97(X2) of differing poses E1 and E2 of distal focal tip 82 relative to a patient heart within X-ray image space 94 as shown in FIGS. 6A-6E are provided to facilitate an understanding of flowchart 110. The acquisition of X-ray images 97 involves a static positioning of C-arm 90 and a dynamic positioning of robot 70 between poses E1 and E2 of distal focal tip 82 within X-ray image space 94 as user-commanded or actuation commanded by calibration controller 107.

Referring to FIGS. 3-5, a stage S112 of flowchart 110 encompasses calibration controller 107 delineating endoscope 80 within an image plane of X-ray image 97(X1). To this end, calibration controller 107 performs a series of steps as follows.

Figure 6A:
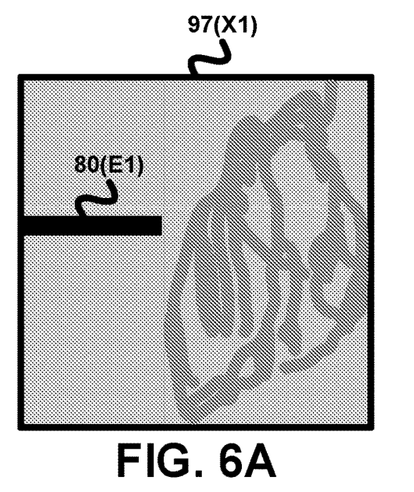
FIGS. 6A-6E illustrates an exemplary execution of the flowchart illustrated in FIG. 5.

First, calibration controller 107 applies a black pixel threshold for selecting a high attenuation area of X-ray image 97(X1) representative of pose E1 of metallic endoscope 80 within X-ray image space as shown in FIG. 6A.

Second, calibration controller 107 executes a contour fitting technique for outlining endoscope 80 with a free-form contour. Examples of the contour fitting technique include, but are not limited to, an active contour technique and a border-following technique. In practice, a minimal contour length may be implemented to address any noise from the black pixel thresholding and a short dimensional nature of the contours.

Figure 6B:
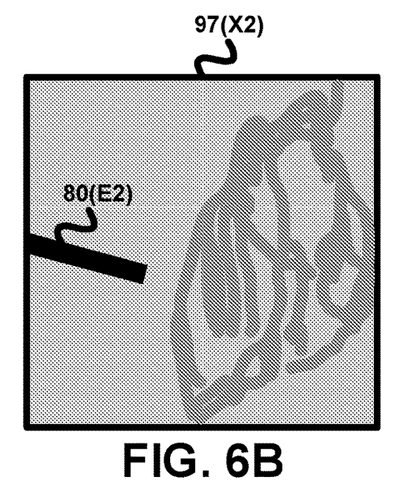
Figure 6C:
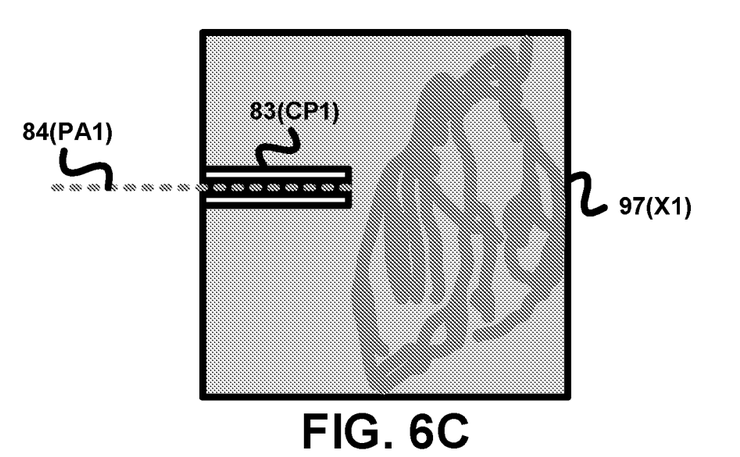

Calibration controller 107 utilizes the free-form contour as an input to a least-squares fitting technique that fits an four (4)-edged contoured polygon 83(CP1) of endoscope pose 80(E1) as shown in FIG. 6C. Of note, this step relies on the fact that endoscope 80 may be viewed as a convex quadrilateral in X-ray image 97(X1) as a function of perspective deformation and plane cutting.

Third, calibration controller 107 computes a principle axis 84(PA1) as shown FIG. 6C extending from a distal tip of contoured polygon 83(CP1) within an image plane of X-ray image 97(X1) for a distance exceeding an estimated RCM length of endoscope 80(E1). Principle axis 84(P1) may be computed in accordance with any known modeling technique including, but not limited to, a Hough Transform.

Fourth, calibration controller 107 computes an average thickness $thx_{E1}$ of endoscope 80(E1) along a perpendicular line of principle axis 84(PA1). The average thickness $thx_{E1}$ of endoscope 80(E1) may be computed in accordance with any known modeling technique including, but not limited to, a Hough Transform.

Fifth, calibration controller 107 detects a distal focal tip of endoscope 80(E1) within X-ray image 97(X1) as positioned within the X-ray coordinate space recording as $t_{E1}=[xt_{E1}, yt_{E1}]$.

Figure 6D:
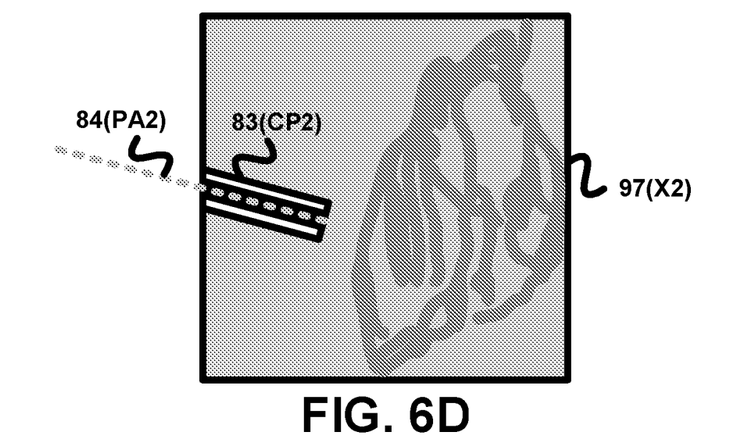

These five (5) steps are repeated for X-ray image 97(X2) as shown in FIG. 6B resulting in a computation of principle axis 84(PA2) as shown FIG. 6D extending from a distal tip of contoured polygon 83(CP2) within an image plane of X-ray image 97(X2), a computation of an n average thickness $thx_{E2}$ of endoscope 80(E2) along a perpendicular line of principle axis 84(PA2), and a detection of the distal focal tip of endoscope 80(E2) as positioned within the X-ray coordinate space recorded as $t_{E2}=[xt_{E2}\ yt_{E2}]$.

A stage S114 of flowchart 114 encompasses calibration controller 107 computing endoscopic RCM length $L_{RCM}$ as shown in FIG. 3. To this end, calibration controller 107 performs a series of steps as follows.

Figure 6E:
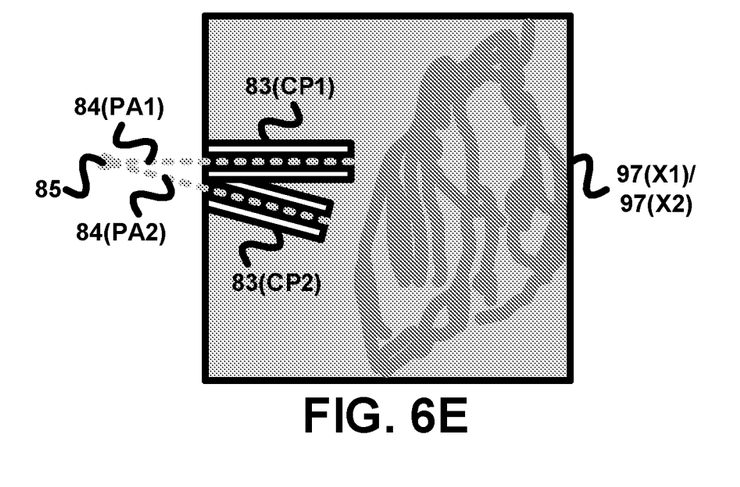

First, calibration controller 107 detects a RCM intersection 85 as shown in FIG. 6E is detected as a point on intersection of principle axis 84(PA1) and principle axis 84(PA2) within the identical image planes of X-ray images 97(X1) and 97(X2).

Second, calibration controller 107 computes a RCM length $L_{RCM1}$ of principle axis 84(PA1) between RCM intersection 85 and the previously detected distal focal tip of endoscope 80(E1), and a RCM length $L_{RCM2}$ of principle axis 84(PA1) between RCM intersection 85 and the previously detected distal focal tip of endoscope 80(E2). In practice, RCM length $L_{RCM1}$ and RCM length $L_{RCM2}$ may be computed as Euclidean distance specified by a number of pixels.

Third, calibration controller 107 computes a depth $D_E$ of endoscope 80 from image intensifier 93 in accordance with the following equation [1]:

$$D_E = f^*(th_E/th_X) \quad [1]$$

where f is a focal length of X-ray image space 94 (known from a SID tag in DICOM),
where $th_E$ is a thickness of endoscope 80 that be known or estimated, and
where $th_X$ is a mean thickness $(thx_{E1}+thx_{E2})/2$ of imaged endoscope 80(E1) and endoscope 80(E2).

In practice, for estimation of the endoscope thickness $th_E$, most commercially known endoscopes have a thickness of 5 mm or 10 mm. Accordingly, calibration controller 107 may compute depths for all possible sizes and then uses additional heuristics to determine the endoscope thickness $th_E$. For example, it may be anticipated that the endoscope 80 will be placed +−200 mm around the center of rotation of the C-arm 91. Using this information, an appropriate endoscope thickness $th_E$ may be selected by calibration controller for estimation purposes. Additionally, intra-operative X-ray controller 105 may compute a patient plane which is added to DICOM information of X-ray modality 90 whereby calibration controller may select an endoscope thickness $th_E$ that matches depth closest to patient plane.

Using an estimation that X-ray imaging is mathematically equivalent to a pin-hole camera, calibration controller 107 computes endoscopic RCM length $L_{RCM}$ in accordance with the following equation [2]:

$$L_{RCM} = {}^*D_E)/L_{RCMX} \quad [2]$$

where f is a focal length of X-ray image space 94 (known from a SID tag in DICOM),
where $D_E$ is a depth of endoscope 80 from image intensifier 93 in accordance with equation [1], and
where $L_{RCMX}$ is a mean RCM length $(L_{RCM1}+L_{RCM2})/2$ of imaged endoscope 80(E1) and endoscope 80(E2).

Upon termination of flowchart 110, calibration controller 107 will have calibrated the RCM length of the robotic endoscope for image integration and robotic endoscope guidance purposes.

FIG. 6 illustrates a flowchart 110 representative of an RCM length calibration method of the present invention.

Figure 7:
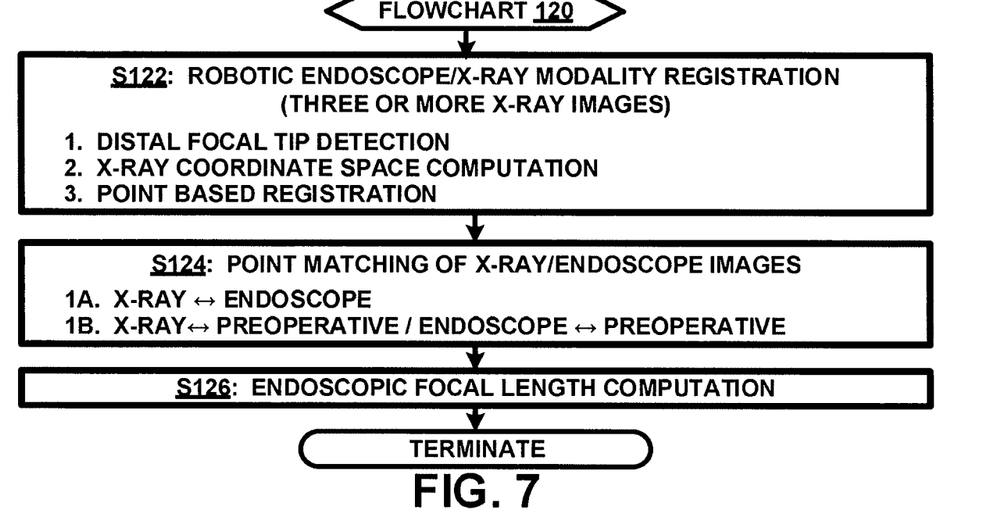
FIG. 7 illustrates a flowchart representative of an exemplary embodiment of an focal length computation method in accordance with the inventive principles of the present invention.

Referring to FIGS. 3, 4 and 7, three (3) exemplary X-ray images 97(X1), 97(X2) and 97 (X3) of differing poses E1, E2 and E3 of distal focal tip 82 relative to a patient heart within X-ray image space 94 as shown in FIGS. 6A-6E are provided to facilitate an understanding of flowchart 110. The acquisition of X-ray images 97 involves a static positioning of C-arm 90 and a dynamic positioning of robot 70 between poses E1-E3 of distal focal tip 82 within X-ray image space 94 as user-commanded or actuation commanded by calibration controller 107.

Figure 8A:
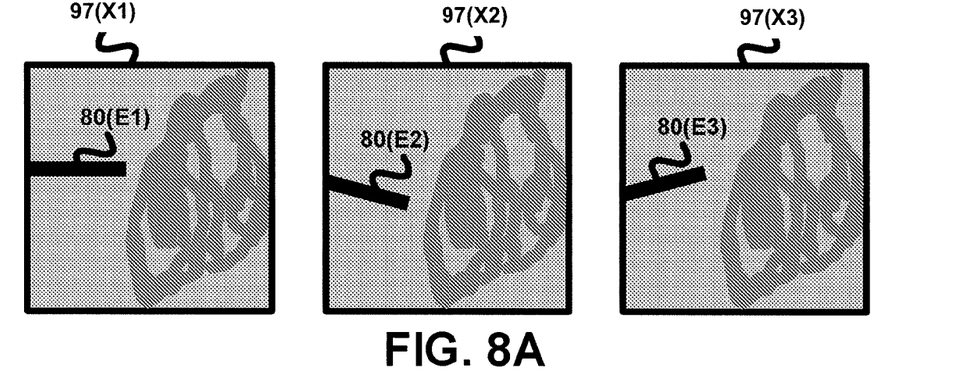
FIGS. 8A-8D illustrate an exemplary execution of the flowchart illustrated in FIG. 7.
Figure 8B:
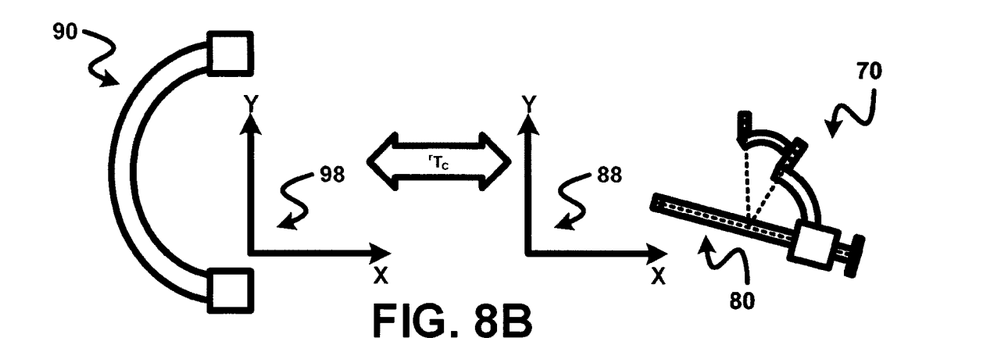

Flowchart 120 is premised on a C-arm coordinate space 98 (FIG. 8B) and X-ray image space 94 (FIG. 4) being related through a known focal length fx and known depth (Z) that is computed as previously described herein in connection with stage S114 (FIG. 5) or estimated from DICOM data in accordance with the following equations [3] and [4]:

$$x = fx^*(X/Z) \quad [3]$$

$$y = fy^*(Y/Z) \quad [4]$$

where x and y are indices in X-ray image space 94 (FIG. 3) and
where X,Y,Z are points C-arm coordinate space 98 (FIG. 8B).

A robot coordinate space and an endoscope coordinate space are not calibrated as a focal length $f_C$ of endoscope 80 is not known. For a 3D point [X,Y,Z] in C-arm coordinate space 98, [xe, ye] are points in the endoscope image space 88 (FIG. 8B), assuming pin-hole model are in accordance with the following equation [5]:

$$\begin{bmatrix} xe \\ ye \\ 1 \end{bmatrix} = \begin{bmatrix} fc & 0 & 0 \\ 0 & fc & 0 \\ 0 & 0 & 1 \end{bmatrix} {}^{\varepsilon}T_c \begin{bmatrix} X \\ Y \\ Z \end{bmatrix} \quad [5]$$

where $^eT_c$ is the coordinate transformation between C-arm coordinates and endoscope coordinates.

A camera is at the distal focal tip of endoscope 80 and a transformation $^eT_r$ for a robot effector tip to the robot RCM 76 (FIG. 3) is known from robot kinematics and RCM length $L_{RCM}$ (FIG. 3) in accordance with the following equation [6]-[26]:

$$T = \begin{bmatrix} x1 & x2 & x3 & x4 \\ x5 & x6 & x7 & x8 \\ x9 & x10 & x11 & x12 \\ 0 & 0 & 0 & 1 \end{bmatrix} \quad [6]$$

$$x1 = k2*m1*s1 + m2*c1*s2 + k1*m2*c2*s1 \quad [7]$$

$$x2 = c1*c2 - k1*s1*s2 \quad [8]$$

$$x3 = k2*c1*s1 - m1*m2*s1 + k1*k2*c2*s1 \quad [9]$$

$$x4 = L*(k2*m1*s1 + m2*c1*s2 + k1*m2*c2*s1) \quad [10]$$

$$x5 = k2*m1*c1 - m2*s1*s2 + k1*m2*c1*c2 \quad [11]$$

$$x6 = -c1*s1 - k1*c1*s2 \quad [12]$$

$$x7 = k1*k2*c1*c2 - k2*s1*s2 - m1*m2*c1 \quad [13]$$

$$x8 = L*(k2*m1*c1 - m2*s1*s2 + k1*m2*c1*c2) \quad [14]$$

$$x9 = k1*k2 - m1*m2*c2 \quad [15]$$

$$x10 = m1*s2 \quad [16]$$

$$x11 = -k1*m2 - k2*m1*c2 \quad [17]$$

$$x12 = L*(k1*k2 - m1*m2*c2) \quad [18]$$

$$k1 = \cos(\theta_1) \quad [19]$$

$$m1 = \sin(\theta_1) \quad [20]$$

$$k2 = \cos(\theta_2) \quad [21]$$

$$m2 = \sin(\theta_2) \quad [22]$$

$$s1 = \sin(\varphi_1) \quad [23]$$

$$c1 = \cos(\varphi_1) \quad [24]$$

$$s2 = \sin(\varphi_2) \quad [25]$$

$$c2 = \cos(\varphi_2) \quad [26]$$

Accordingly, transformation $^eT_c$ may be represented by the following equation [27]:

$$^eT_c = {^tT_c} = {^tT_r}{^rT_c} \quad [27]$$

where $^tT_c$ is a transformation from C-arm 90 to robot effector tip 75, where $^tT_r$ is a transformation from robot 70 to robot effector tip 75, and where $^rT_c$ is a transformation between C-arm 90 and robot 70.

In order to compute focal length fc, flowchart 120 utilizes point matching between the X-ray images and the endoscope images [x y] ↔ [xe ye], $^rT_c$ and 3D points X, Y, Z that may be retrieved from a C-arm imaging model.

Specifically, a stage S122 of flowchart 120 encompasses calibration controller 107 registering robot 70 to C-arm 94. This registration is achieved using image-based method involving three (3) X-ray images 96 (FIG. 8A) with two data points each (x and y) to determine six (6) unknown variables (three (3) rotations and three (3) translations).

First, for every X-ray image 97, calibration controller 107 detects a position of the distal focal tip of endoscope 80 in X-ray image space 94 and records the detected positions in a robot coordinate space.

Second, calibration controller 107 computes positions of the distal focal tip of endoscope 80 in C-arm 3D space 98 from a model of C-arm 90 and known depth.

Third, calibration controller 107 performs a known point-based registration from the detected/computed positions. In practice, calibration controller 107 may indicate a current residual error of registration to a workstation user/operator, whereby the user/operator may selectively acquire additional X-ray images to minimize the residual error.

Figure 8C:
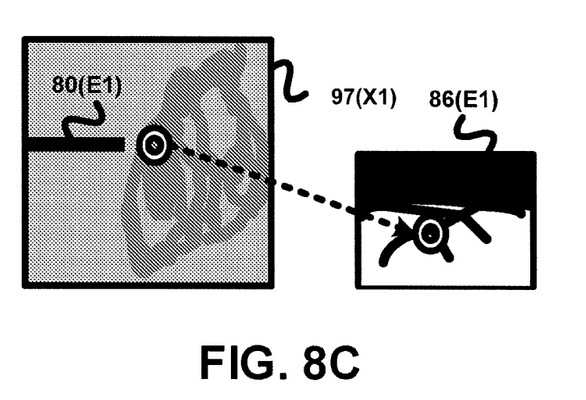
Figure 8D:
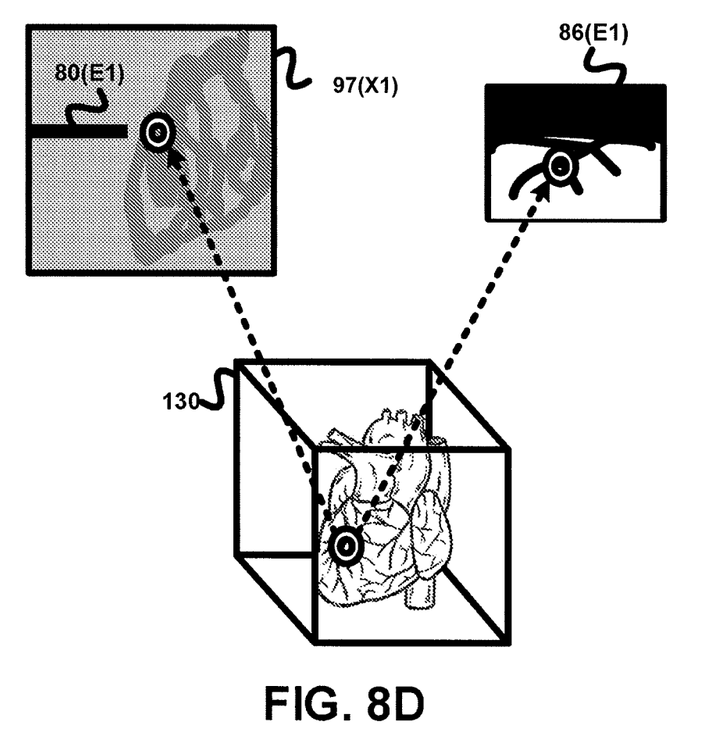

A stage S124 of flowchart 120 encompasses calibration controller 107 executing a point matching ([x y]↔[xe ye]) between X-ray images and endoscope images. In practice, at least one point visible in both images has to be identified. This identification may be done manually, such as, for example, by marking an arterial bifurcation in both an X-ray image 97 and an endoscope image 86 as shown in FIG. 8C. Alternatively, if the X-ray images and the endoscope images are registered to a preoperative image (e.g. a MRI or CT image), then calibration controller 107 may identify visible points in both images, such as, for example, a point of a registered MRI image 130 being identified by calibration controller 107 in X-ray image 97 and endoscope image 86 as shown in FIG. 8D.

A stage S126 of flowchart 120 encompasses calibration controller 107 computing the endoscopic focal length fc is accordance with equation in accordance with the aforementioned equation [5] from the data computed during stages S122 and S124:

$$\begin{bmatrix} xe \\ ye \\ 1 \end{bmatrix} = \begin{bmatrix} fc & 0 & 0 \\ 0 & fc & 0 \\ 0 & 0 & 1 \end{bmatrix} {^eT_c} \begin{bmatrix} X \\ Y \\ Z \end{bmatrix} \quad [5]$$

Referring to FIGS. 5 and 7, In practice, calibration controller 107 may sequentially or concurrently execute flowcharts 110 and 120. Furthermore, calibration controller 107 executes initial length calibrations that may be recalibrated or refined with additional X-ray images.

Figure 9A:
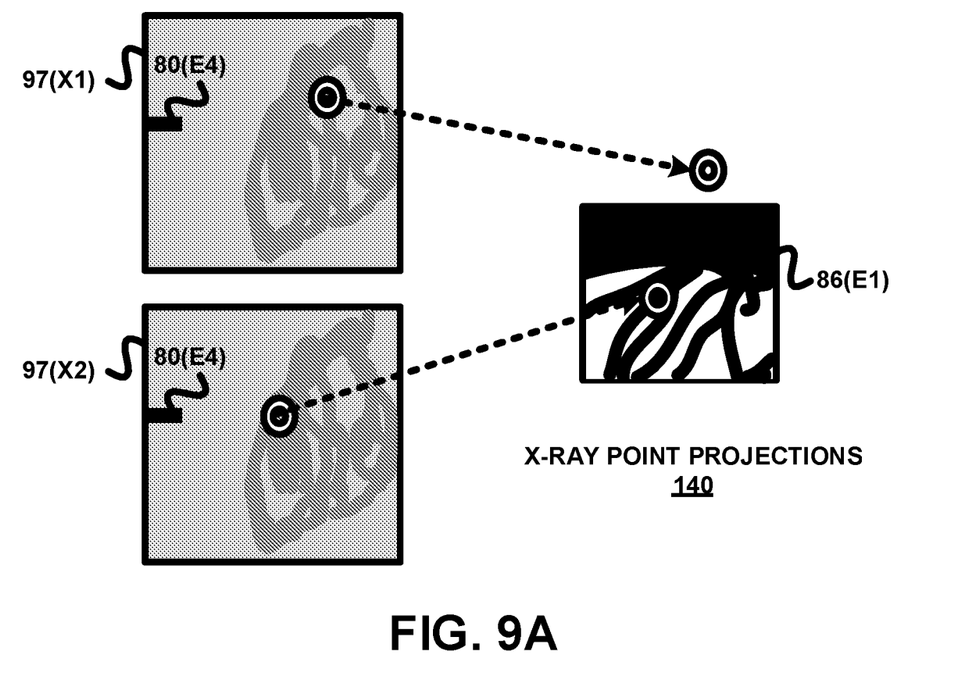
FIGS. 9A-9D illustrate exemplary image integrations of X-ray images and an endoscope image in accordance with the inventive principles of the present invention.
Figure 9B:
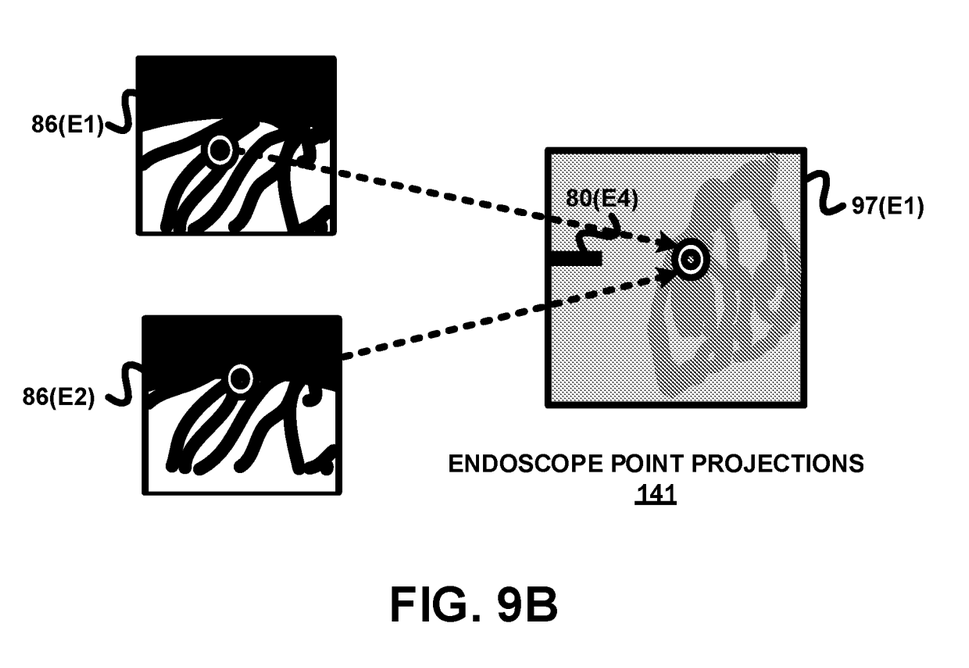
Figure 9C:
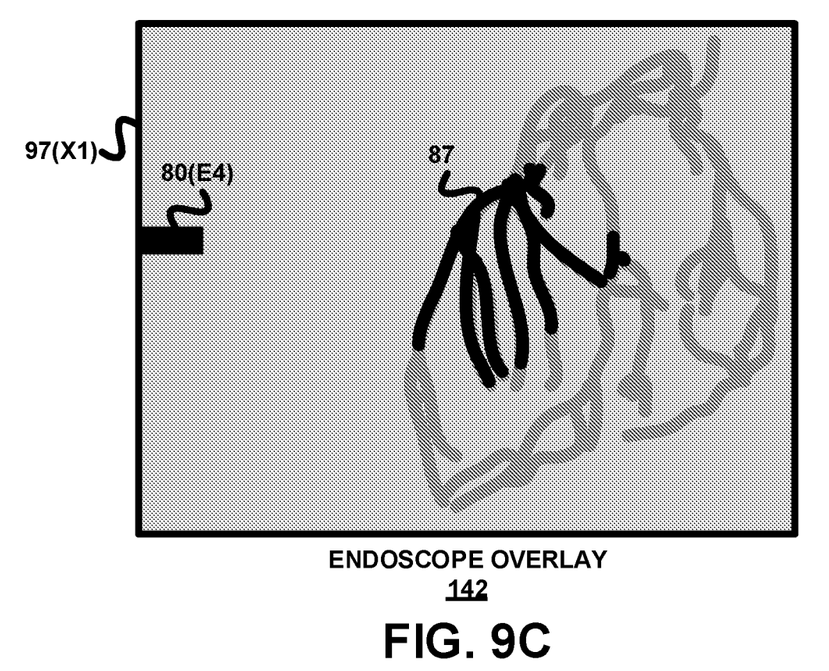
Figure 9D:
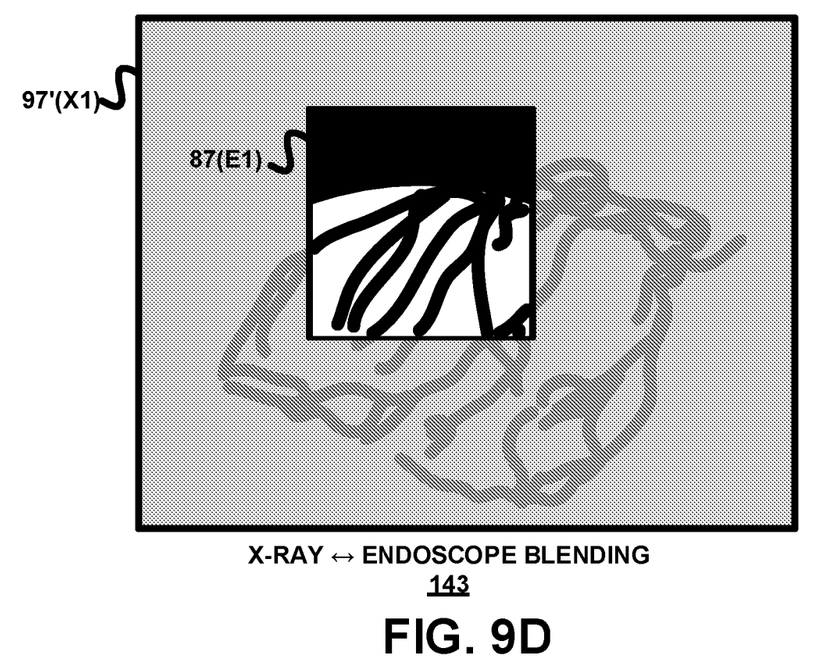

As previously described for phase 12 (FIG. 1), from the length calibrations, known image integration technique may be implemented by X-ray point projections 140 as exemplary shown in FIG. 9A, endoscope point projections 141 as exemplary shown in FIG. 9B, an endoscope overlay on X-ray 142 as exemplary shown in FIG. 9C, and an X-ray/endoscope image blending 143 as exemplary shown in FIG. 9D.

Specifically, referring to FIG. 9A, X-ray point projections 140 involves target points user-identified in X-ray images 97(X1) and 97(X2) that are triangulated by calibration controller 107 into the C-arm coordinate space and projected into the image space of endoscope 80 using pin-hole models of both imaging modalities and known calibration of the endoscope 80. For example as shown, a stenosis identified in X-ray space can be projected on endoscope image space to allow identification of bypass site in endoscope images. This projection may be in the field-of-view of endoscope or outside, projected on the extended plane of the image.

Referring to FIG. 9B, using the same projection method, the points from two endoscope images 86 are projected into X-ray image 97. For this type of projection, calibration controller 107 guides the X-ray image acquisition by computing optimal position of C-arm 90 whereby a particular part of the endoscope image is acquired with minimum foreshortening or found with minimal number of X-ray acquisitions.

Referring to FIG. 9C, an overlay 87 of the endoscope image is computed and upon at least one motion of robot 70, overlay 87 is recomputed in the C-arm coordinate space and projected onto the X-ray image 97 (X1).

Referring to FIG. 9D, an X-ray image 97' and an endoscope image 87 are blended together in the same coordinate frame. As shown, calibration controller 107 deforms X-ray image 97 (FIG. 9C) using a perspective transformation so that X-ray image 97' is viewed from a perspective of endoscope image 87. If it is not practical to orient the C-arm 90 the same way as endoscope 80 (e.g., endoscope 80 is obstructing x-ray images from that C-arm orientation), then this visualization is helpful in extending the field of view of endoscope 80.

As previously described for phase 13 (FIG. 1), from the length calibrations and image integration, robotic endoscope 70/80 (FIG. 3) may now be guided from the X-ray images by a user selection of a target point in an X-ray image whereby the robotic endoscope will be positioned to center the target point in the endoscope image.

Referring to FIGS. 1-9, those having ordinary skill in the art will appreciate numerous benefits of the present invention including, but not limited to, a robust means for calibrating a robotic endoscope with minimal workflow stoppage.

Furthermore, as one having ordinary skill in the art will appreciate in view of the teachings provided herein, features, elements, components, etc. described in the present disclosure/specification and/or depicted in the FIGS. 1-9 may be implemented in various combinations of electronic components/circuitry, hardware, executable software and executable firmware and provide functions which may be combined in a single element or multiple elements. For example, the functions of the various features, elements, components, etc. shown/illustrated/depicted in the FIGS. 1-9 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive calibration procedures for a robotic endoscope within an X-ray suite for minimally invasive procedures, (which embodiments are intended to be illustrative and not limiting), it is noted that modifications and variations can be made by persons having ordinary skill in the art in light of the teachings provided herein, including the FIGS. 1-9. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A workstation for calibrating a robotic instrument having a distal tip within an X-ray image space of an X-ray modality, the workstation comprising:
   a calibration controller configured to calibrate a remote center of motion (RCM) length of the robotic instrument responsive to a generation by the X-ray modality of a plurality of X-ray images of different poses of the distal tip of the robotic instrument within the X-ray image space; and
   a robotic instrument controller in communication with the calibration controller, the robotic instrument controller configured to control a guidance of the robotic instrument within the X-ray image space as a function of the calibration by the calibration controller of the RCM length of the robotic instrument; and wherein the calibration controller is further configured to calibrate a focal length of the robotic instrument responsive to the generation by the X-ray modality of the X-ray images of different poses of the distal tip of the robotic instrument within the X-ray image space and further responsive to a generation by the robotic instrument of at least one endoscope image of the X-ray image space.

2. The workstation of claim 1, wherein the calibration controller is configured to control the calibration of the RCM length of the robotic instrument as the X-ray images are being generated by the X-ray modality.

3. The workstation of claim 1, wherein a control of the calibration by the calibration controller of the RCM length of the robotic instrument includes:

the calibration controller operable to compute the RCM length of the robotic instrument responsive to at least two of the X-ray images.

4. The workstation of claim 3, wherein a computation by the calibration controller of the RCM length of the robotic instrument includes:

the calibration controller configured to delineate the robotic instrument within an image plane of each of the at least two of the X-ray images.

5. The workstation of claim 4, wherein the computation by the calibration controller of the RCM length of the robotic instrument further includes:

the calibration controller configured to compute the RCM length of the robotic instrument as a function of an intersection of the robotic instrument as delineated within the image planes of the at least two X-ray images.

6. The workstation of claim 1, wherein the robotic instrument includes an endoscope.

7. The workstation of claim 6, wherein the calibration controller is configured to control the calibration of the focal length of the robotic instrument as the X-ray images are being generated by the X-ray modality and as the at least one endoscope image is being generated by the endoscope.

8. The workstation of claim 7, wherein the robotic instrument controller is further configured to control the guidance of the endoscope within the X-ray image space as a function of the focal length of the endoscope.

9. The workstation of claim 6, wherein the calibration controller is further configured to integrate the X-ray images and the at least one endoscope image as a function of the calibration of the focal length of the endoscope.

10. The workstation of claim 9, further comprising:

a display controller in communication with the calibration controller and configured to control a display of the integrated X-ray and endoscope images.

11. The workstation of claim 6, wherein the calibration controller is configured to compute the focal length of the endoscope responsive to at least three of the X-ray images and the at least one endoscope image.

12. The workstation of claim 11, wherein the calibration controller is further configured to register the X-ray imaging modality to the endoscope responsive to the at least three X-ray images.

13. The workstation of claim 12, wherein the calibration controller is configured to execute a point matching between the at least three X-ray images and the at least one endoscope image based on a registration of the X-ray imaging modality to the endoscope.

14. A workstation for calibrating a robotic instrument including an endoscope having a distal tip within an X-ray image space of an X-ray modality, the workstation comprising:

one or more processors configured to:
calibrate a remote center of motion (RCM) length of the robotic instrument responsive to a generation by the X-ray modality of at least two X-ray images of different poses of the distal tip of the robotic instrument within the X-ray image space, and compute a focal length of the endoscope as function of a registration of the X-ray imaging modality to the robotic instrument and a point matching between at least three X-ray images and the at least one endoscope image; and a robotic instrument controller in communication with the one or more processors and configured to control a guidance of the endoscope within the X-ray image space based on the RCM length of the endoscope and the focal length of the endoscope.

15. A calibration controller for calibrating a robotic instrument including a robotically controlled endoscope having a distal tip within an X-ray image space of an X-ray modality, the calibration controller comprising:

a robotic instrument calibrator configured to calibrate a remote center of motion (RCM) length and a focal length of the robotically controlled endoscope, the focal length being calculated by generating by the X-ray modality at least three X-ray images of different poses of the distal tip of the robotically controlled endoscope within the X-ray image space, generating at least one endoscope image of the X-ray image space with the robotically controlled endoscope and point matching the at least three X-ray images and the at least one endoscope image; and an image integrator operable in communication with the robotic instrument calibrator to integrate the at least three X-ray images and the at least one endoscope image responsive to the calibration by the robotic instrument calibrator of the RCM length and the focal length of the robotic instrument.

16. A calibration method for calibrating a robotic instrument having a robotically controlled endoscope having a distal tip within an X-ray image space of an X-ray modality, the calibration method comprising:

with the X-ray modality, generating at least three X-ray images of different poses of the distal tip of the robotically controlled endoscope within the X-ray image space;

point matching the at least three x-ray images and at least one endoscopic image;

calculating a focal length of the robotically controlled endoscope based on the point matching;

calibrating a remote center of motion (RCM) length and the focal length of the robotically controlled endoscope; and with the robotically controlled endoscope, generating at least one endoscope image.

17. The calibration method of claim 16, further comprising at least one of:

integrating the at least three X-ray images and the at least one endoscope image as a function of the calibration of the RCM length and the focal length of the robotically controlled endoscope;

displaying the integrated X-ray images and endoscope images; and controlling a guidance of the robotically controlled endoscope within the X-ray image space as a function of the calibration of the RCM length and the focal length the robotically controlled endoscope.

18. The workstation of claim 1, wherein the calibration controller point matches the plurality of X-ray images and the at least one endoscope image, the focal length of the endoscope being computed as a function of the point matched X-ray and endoscope images.

* * * * *